United States Patent [19]
Lundquist

[11] Patent Number: 5,315,996
[45] Date of Patent: May 31, 1994

[54] TORQUABLE CATHETER AND METHOD

[76] Inventor: Ingemar H. Lundquist, 17 Mile Drive at The Dunes, Pebble Beach, Calif. 93953

[21] Appl. No.: 6,207

[22] Filed: Jan. 19, 1993

Related U.S. Application Data

[63] Continuation of Ser. No. 918,922, Jul. 22, 1992, abandoned, which is a continuation of Ser. No. 657,106, Feb. 15, 1991, abandoned.

[51] Int. Cl.$^5$ .............................................. A61B 5/04
[52] U.S. Cl. ................................... 128/642; 607/122; 607/119
[58] Field of Search .................. 128/642, 784–786, 128/774, 772, 4, 6; 604/95, 96, 280, 282

[56] References Cited

U.S. PATENT DOCUMENTS

| | | | |
|---|---|---|---|
| 4,273,111 | 6/1981 | Tsukaya | 128/772 |
| 4,580,551 | 4/1986 | Siegmund et al. | 128/4 |
| 4,660,571 | 4/1987 | Hess et al. | 128/642 |
| 4,664,113 | 5/1987 | Frisbie et al. | 128/772 |
| 4,911,148 | 3/1990 | Sosnowski et al. | 128/4 |
| 4,920,980 | 5/1990 | Jackowski | 128/786 |
| 4,940,062 | 7/1990 | Hampton et al. | 128/772 |
| 4,941,455 | 7/1990 | Watanabe et al. | 128/4 |
| 4,942,866 | 7/1990 | Usami | 128/4 |
| 4,960,134 | 10/1990 | Webster, Jr. | 128/642 |
| 4,998,923 | 3/1991 | Samson et al. | 604/95 |
| 5,037,391 | 8/1991 | Hammerslag et al. | 604/95 |

*Primary Examiner*—Lee S. Cohen
*Assistant Examiner*—Jeffrey R. Jastrzab
*Attorney, Agent, or Firm*—Flehr, Hohbach, Test, Albritton & Herbert

[57] ABSTRACT

Catheter having a high torque capability adapted to be inserted into and through a lumen of a blood vessel comprising a flexible elongate tubular shaft having proximal and distal extremities. The shaft is comprised of a torque tube extending substantially the entire length of the shaft. The torque tube has a cylindrical wall with at least one flexible portion therein with the flexible portion being characterized in that at least one slot is provided in the cylindrical wall subtending an angle of less than 360°. A flexible sleeve encloses the torque tube and serves to cover the flexible portion while permitting the torque tube to bend in the vicinity of the slot a predetermined amount which is less than that which would create a permanent strain in the torque tube.

32 Claims, 3 Drawing Sheets

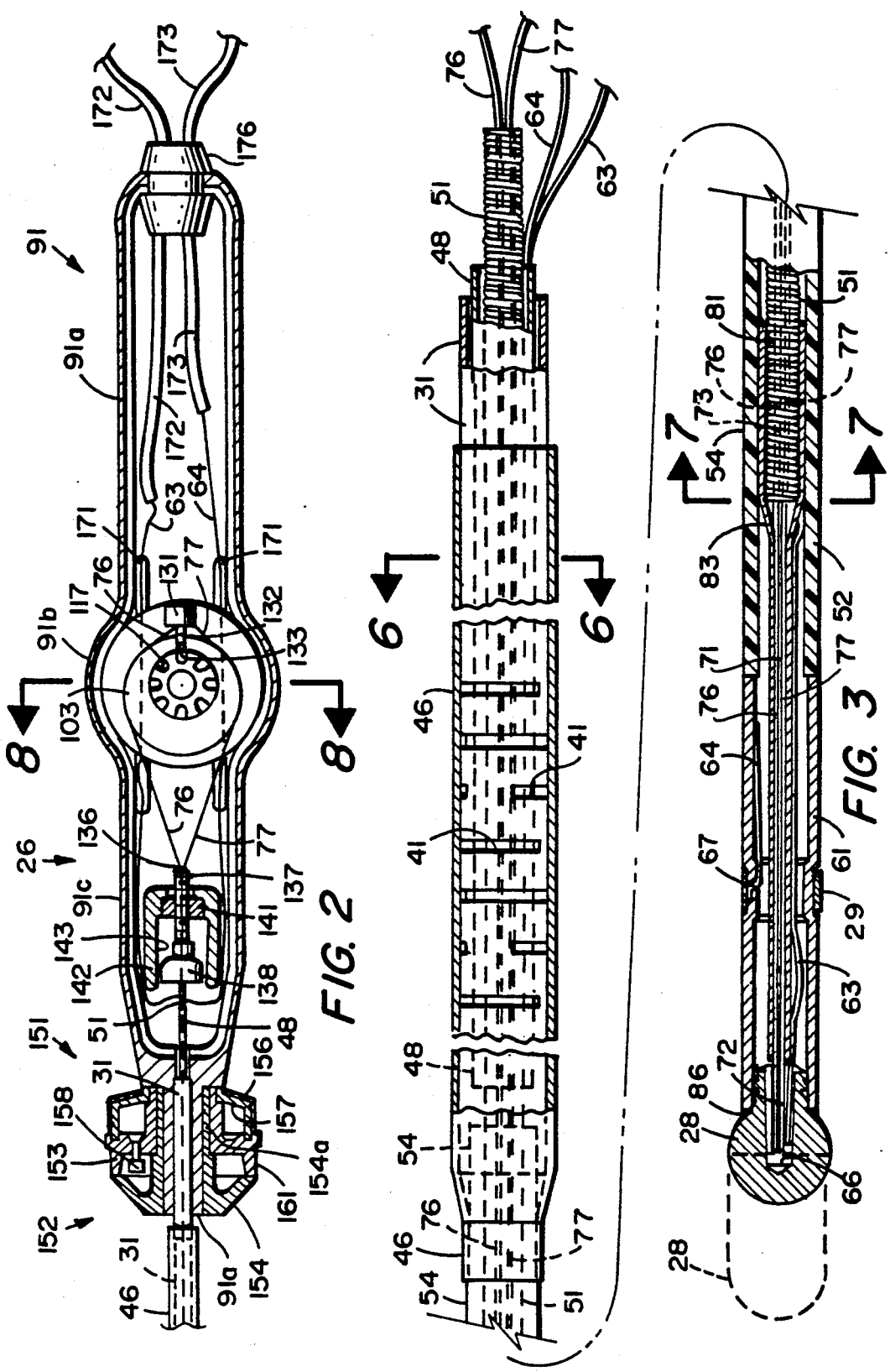

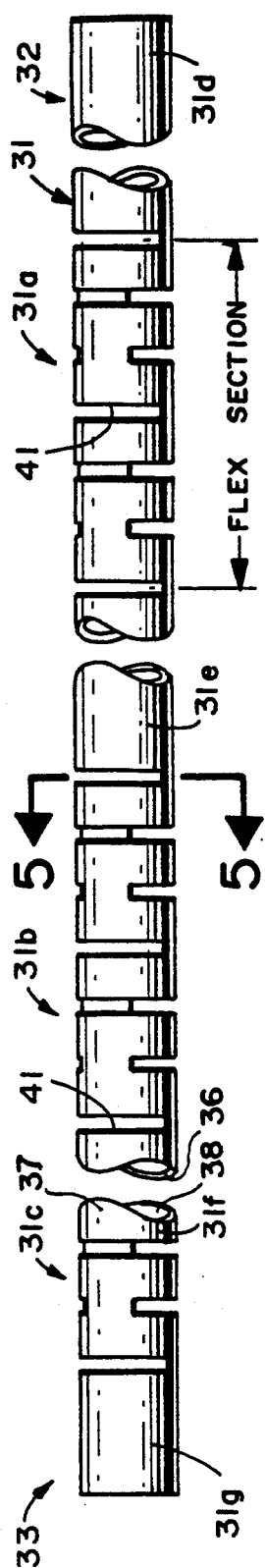
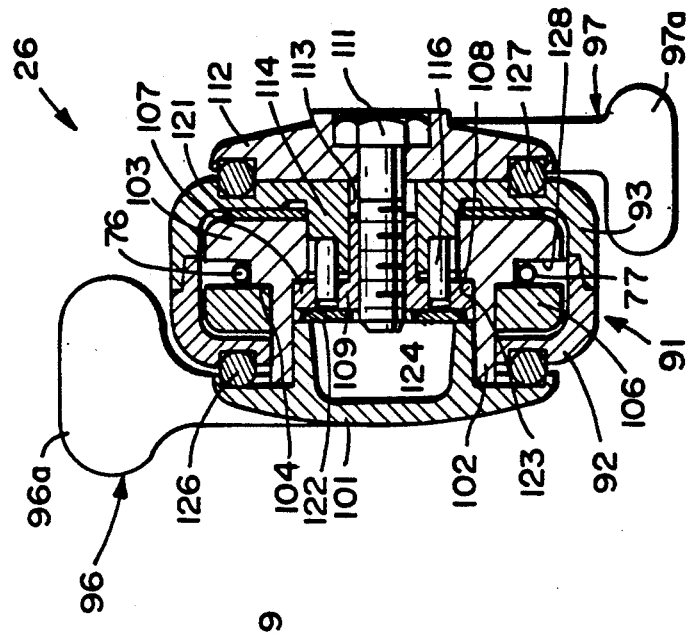
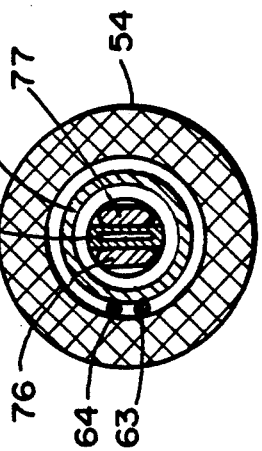
FIG. 4
FIG. 5
FIG. 6
FIG. 7
FIG. 8

TORQUABLE CATHETER AND METHOD

This is a continuation of application Ser. No. 07/918,922 filed Jul. 22, 1992 now abandoned which is a continuation of application Ser. No. 07/657,106 filed Feb. 15, 1991 now abandoned.

This invention relates to a torquable catheter and method and more particularly to a torquable catheter and method which has a steerable tip.

In the past, steerable catheters have heretofore been provided to facilitate maneuvering in blood vessels. However, in the past with such devices it has been difficult to achieve a substantially one to one rate of movement for the proximal and distal extremities of the catheter. There is therefore a need for a new and improved catheter which can achieve such a one-to-one ratio and a method for making the same.

In general, it is an object of the present invention to provide a torquable catheter and method in which a substantially one to one ratio of movement between proximal and distal extremities of the catheter can be achieved.

Another object of the invention is to provide a catheter and method of the above character which has the desired degree if flexibility.

Another object of the invention is to provide a catheter and method of the above character which can be utilized in a blood vessel.

Another object of the invention is to provide a catheter and method of the above character in which the distal extremity can be steered.

Another object of the present invention is to provide a catheter and method of the above character which is particularly adapted for use in mapping and/or ablation procedures in the heart.

Another object of the invention is to provide a catheter and method of the above character which incorporates a scale for indicating the amount of bend which has been provided in the distal extremity of the catheter.

Another object of the invention is to provide a catheter and method of the above character in which the amount of rotation or twist of the catheter from a reference position can be ascertained by reading a scale associated with a bubble chamber incorporated in the handle of the catheter.

Additional objects and features of the invention will appear from the following description of the particular embodiment as set forth in detail in conjunction with the accompanying drawings:

FIG. 2 is a plan view in cross-section of the steering handle of the catheter shown in FIG. 1.

FIG. 3 is a cross sectional view of the catheter shaft and distal extremity of the catheter shown in FIG. 1.

FIG. 4 is an elevational view of the torque tube utilized in the catheter shown in FIG. 1.

FIG. 5 is a cross-sectional view taken along the line 5—5 of FIG. 4.

FIG. 6 is a cross-sectional view taken along the line 6—6 of FIG. 3.

FIG. 7 is a cross sectional view taken along the line 7—7 of FIG. 3.

FIG. 8 is a cross sectional view taken along the line 8—8 of FIG. 2.

Figure 1:
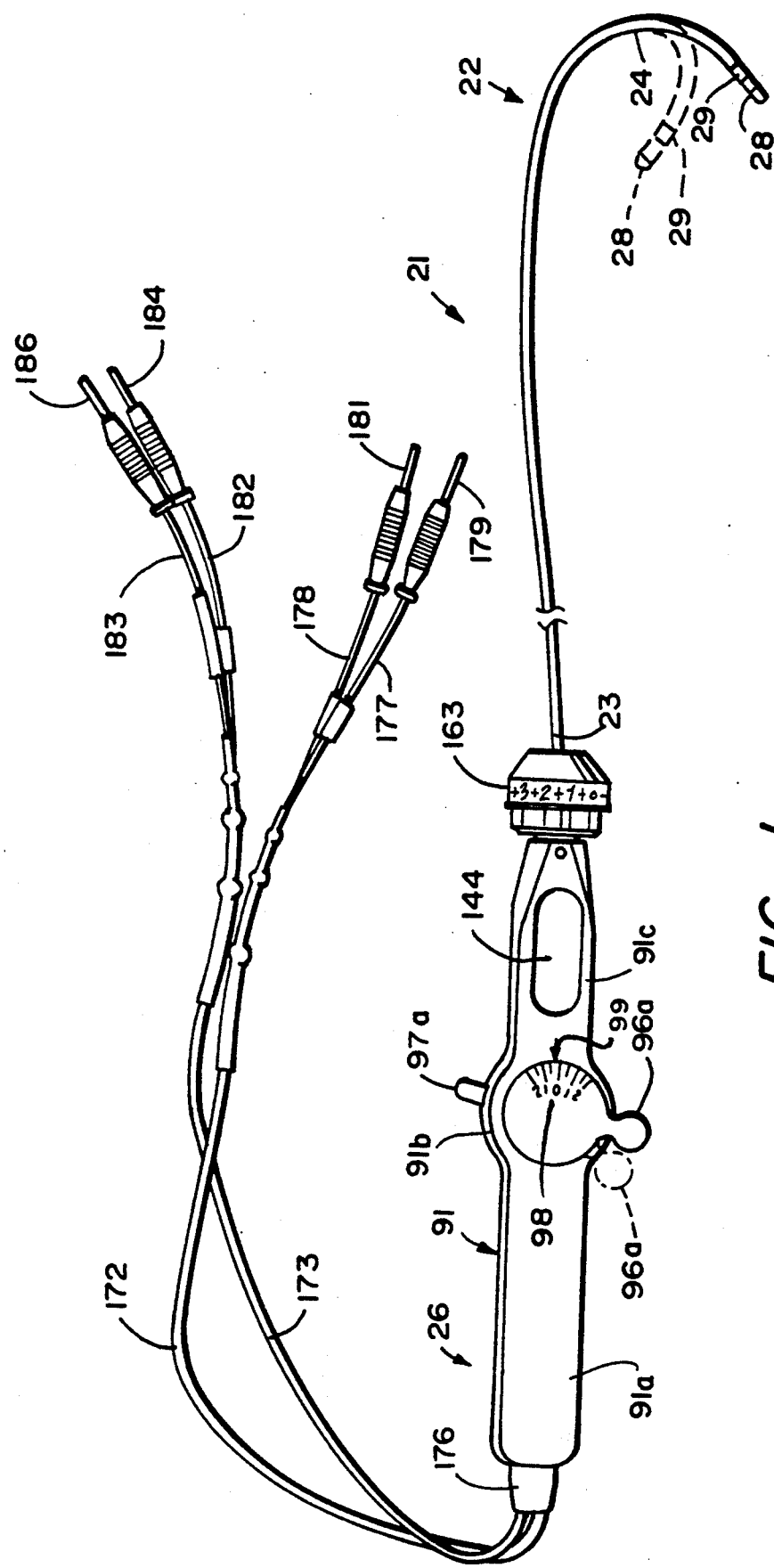
FIG. 1 is a plan view of a torquable catheter incorporating the present invention.

In general, the torquable catheter of the present invention is adapted to be inserted into and through a lumen of a blood vessel and comprises a flexible elongate tube or shaft having proximal and distal extremities and having a lumen extending therethrough. The shaft is comprised of a torque tube extending the length of the shaft. The torque tube has a cylindrical wall, with at least one flexible portion therein. The flexible portion characterized in that a plurality of longitudinally spaced apart slots are provided in the cylindrical wall which extend through the wall with each of the slots subtending less then 360°. A flexible sleeve extends over the torque tube and encases the torque tube which permits flexing of the torque tube within the elastic limits of the torque tube.

More particularly, as shown in the drawings, the torquable catheter 21 incorporating the present invention consists of a flexible elongate tube or shaft 22 having proximal and distal extremities 23 and 24. A steering handle 26 is secured to the proximal extremity 23. At least one electrode, a first electrode 28 and preferably an additional or second electrode 29 are mounted on the distal extremity 24 in a manner hereinafter described.

The catheter shaft 22 is comprised of a flexible elongate torque tube 31 which extends from the steering handle 26 to near the distal extremity 24 of the catheter shaft. The torque tube 31 is formed of a suitable material such as 13 gauge thin wall stainless steel. Such stainless steel tube 31 has an outer diameter of 0.095" and inside diameter of 0.077" to provide a wall thickness of 0.009". It should be appreciated that it is within the scope of this invention to utilize torque tubes of various diameters and wall thicknesses depending upon the torque capability required for the torque tube 31. For example, utilizing the same diameter, a different wall thickness ranging from 0.007" to 0.012" can be provided. The torque tube can have a suitable length as determined by the length of the catheter 21.

By way of example, a catheter constructed in accordance with the present invention had a torque tube 31 having a length of 38". A torque tube 31 having such a length is elongate and is flexible. However, to impart additional flexibility to the torque tube 31 while, retaining its high torque capabilities, the torque tube 31 is provided with at least one flexible portion intermediate its ends and typically is provided with a plurality of such flexible portions. As shown in FIG. 4, three such flexible portions identified as 31a, 31b and 31c have been provided. These flexible portions 31a, 31b and 31c are spaced apart longitudinally of the torque tube 31 between the proximal and distal extremities 32 and 33 so that there remains solid portions 31d, 31e, 31f and 31g. The solid portion 31d can be characterized as a shaft portion, the portions 31e and 31f as intermediate portions and portion 31g as a tip portion. The torque tube 31 is formed by an elongate cylindrical wall 36 which has an outer cylindrical surface 37. It also has an inner cylindrical surface 38 which defines a lumen 39 which extends the length of the torque tube 31.

Each of the flexible portions 31a, 31b and 31c is comprised of at least one slot and preferably a plurality of slots 41 which extend through the cylindrical wall 36 and are spaced longitudinally of the torque tube 31. The slots 41 are radially offset with respect to each other. Each of the slots subtends less than one circumference of the tube wall 36 or in other words less than 360°. Preferably the slots subtend an angle ranging from 270° to 300°. Thus, as shown in FIG. 5, there is provided a slot 41 which is cut into the cylindrical wall until the inside surface 38 on the other side of the of the wall 36 is reached so that there remains material in the wall 36 which extends over 0.064" or approximately 60°. The slots are radially offset with respect to each other by a suitable angle as for example 120°. However, these radial offsets can range from 30° to 120°. The slots 41 shown in the drawings extend transversely or normal to the longitudinal axis of the torque tube 31.

It should be appreciated, however, that if desired, the slots 41 can be formed at an angle from portions of a helix.

The distance between each slot 41 in a flexible portion can be defined as the pitch and can range from 0.03" to 0.09" and preferably approximately 0.055". A flexible length of the torque tube 31 can be considered to be a flexible portion associated with a solid wall portion as for example portions 31f and 31c.

The desired degree of flexibility in a flex portion can be varied by providing fewer or more slots 41 in a flex portion. Thus, there can be provided as few as a single slot to a total of 10 or more slots with the typical flex portion having seven slots as shown in the drawings. In order to give the flexibility of movement of a universal joint at least three slots offset by 120° increments should be provided. Alternatively, four slots offset in 45° can be provided to provide such motion flex portion will permit approximately 30° of bending on a ⅝" inside radius. Thus, two flex portions with no solid tubing in between would permit approximately 60° of bending on a ⅝" inside radius.

By way of example, a torque tube 31 having a length of 38" and made in accordance with the present invention had a tip portion 31g with has a length of 1/5". It had a first flex group comprised of five flex portions each having a length of 1" for a total of 5", a second flex group of seven flex lengths of 1½" each for a total of 10½" and a third flex group of 10 flex lengths of 2" each for a total of 20" and a shaft portion 31d having a length of 2". A flex length can be comprised of a single flex section plus a solid length of tubing ending at the first slot in the next flex section. By providing such flex groups, it has been found that the desired flexibility can be achieved for the catheter while still retaining high torque capabilities of the torque tube 31. It should be appreciated that additional flexibility can be obtained in the catheter by providing additional slots in the torque tube 31 with some sacrifice in the torque capabilities of the torque tube.

A thin walled shrink tubing 46 made of a suitable material such as a polyolefin encapsulates the outer surface 37 of the torque tube 31. The tubing 46 is applied by slipping it over the outer surface 37 of the torque tube 31 and then heating the same to cause it to shrink tightly onto the torque tube 31 to be in direct contact therewith. The shrink tubing 46 serves several purposes. It serves to provide a protective wall for the catheter which encloses the torque tube 31 so as to provide a smooth outer surface with low friction to engage the wall of the vessel of the patient into which the catheter 21 is introduced. It also serves to prevent undue separation of the segments on the opposite sides of the slots 41.

The shrink tubing 46 is very flexible and permits desired flexing of the torque tube 31 but prevents undue bending or stress in the material of the side wall in any one slot and thereby prevents the placement of a permanent strain in any portion of the tube. In other words, the tubing 46 prevents bending or flexing of the torque tube beyond the point from which it will not yieldably return to its original configuration. The tubing 46 also serves to prevent blood or any other liquid in the lumen in which the catheter is introduced from entering into the slots 41 and causing possible clotting. The shrink tubing 46 can have an appropriate wall thickness such as 0.002" with a wall thickness ranging from 0.001 to 0.004".

A sleeve or tube 48 formed of a suitable insulating material such as a plastic as for example a polyamide is disposed within the torque tube 31 (see FIG. 6) which extends the length of the torque tube 31. An elongate tightly coiled coil spring 51 is disposed within the sleeve or tube 48 and also extends the length of the torque tube 41. The coil spring 51 is formed of a spring steel wire rectangular in cross section. It can have suitable inside and outside diameters, as for example an outside diameter of 0.0360" and an inside diameter of 0.0260" and a wall thickness of 0.005". The wire for the coil spring 51 can have side dimensions of 0.005" for a square cross section. The use of square wire for the coil spring 51 also serves to prevent collapsing of the turns of the coil during flexing and compression of coil spring 51.

The distal extremity of the coil spring 51 extends beyond the distal extremity of the tube 31 and extends into a flexible braided tubular member 54 formed of a suitable material such as a plastic with braided wire embedded therein. The braided member 54 extends within the shrink tubing 46 and into the distal extremity of the torque tube 31 as shown in FIG. 3 and is secured to the torque tube 31 by suitable means such as an adhesive so that the braided tubular member 54 rotates with the torque tube 31. The distal extremity of the insulating tube 48 extends near the distal to extremity of the torque tube 31. The braided tubular member 54 extends distally beyond the distal extremity of the coil spring 51 and is bonded by a suitable means such as an adhesive (not shown) to a soft plastic tubing 61.

The tubing 61 carries the electrodes utilized in connection with the present catheter and as shown also serves to mount a first or tip electrode 28 and a second or ring electrode 29 hereinbefore described. Conductors 63 and 64 are connected to the electrodes 28 and 29. Conductor 63 extends into a recess 66 in the tip electrode 28 and conductor 64 extends through a hole 67 makes contact with the ring electrode 29.

Means is provided for causing bending of the distal extremity of the catheter and consists of a bendable flat spring element 71 (see FIG. 7) which has a distal extremity 72 that is seated in the recess 66 provided in the tip electrode 28. The spring element 71 is also provided with a proximal extremity 73 seated in slots (not shown) in the distal extremity of the coil spring 51 so that the coil spring 51 serves as a substantially incompressible element in the catheter 21. First and second pull wires or elements 76 and 77 have their distal extremities bonded to opposite sides of the flat spring element 71. The pull wires or elements 76 and 77 extend into the proximal extremity of the catheter 21 by extending through the lumen 81 provided interiorly of the coil spring 51.

Another shrink tube 83 is provided and extends from the distal extremity of the coil spring 51. The tube 83 surrounds the first and second pull wires 76 and 77 and the bendable spring element 71 and extends to the tip electrode 28. The recess or cavity 66 of the electrode 28 is filled with a suitable conducting material such as solder which serves to provide electrical contact to the leads 63 and also to hold the pull wires 76 and 77 and the bendable flat spring element 71 in place. An adhesive 86 can be provided in the space between the distal extremity of the tubing 61 and the outer surface of the tip electrode 28. The tip electrode 28 can have a suitable conformation such as spherical or elongate with a hemisphere tip, as shown.

The conductors or leads 63 and 64 for the electrodes 28 and 29 extend into the proximal extremity of the catheter 21 between the coil spring 51 and the braided tubular member 54 and thereafter between the coil spring 51 and the inner surface of the insulating tube 48.

As shown, the first and second pull wires 76 and 77 can be in the form of flat wires to minimize their space requirements. These first and second pull wires 76 and 77 can be identified as right and left pull wires extend to the proximal extremity of the catheter 21 through the torque tube 31 as do the conductors 63 and 64 into the steering handle 26.

The steering handle 26 consists of a housing 91 formed of a suitable material such as plastic. The housing 91 is formed of two mating parts 92 and 93 (see FIG. 8) which form two halves of the housing and which are fastened together by ultrasonic welding or an adhesive (see FIGS. 1 and 2). This housing 91 has a handle portion 91a which is elongate and which is adapted to be engaged by the hand of the user. The housing is provided with a large cylindrical portion 91b which has a steering lever 96 and a locking lever 97 rotatably mounted thereon. The handles 96 and 97 are provided with enlarged finger engaging portions 96a and 97a respectively which extend slightly outward of the cylindrical portion 91b and extend inwardly diametrically of the housing as shown particularly in FIG. 8. The housing 91 is also provided with an elongate portion 91 which receives the proximal extremity of the shaft 22. Means is provided within the housing 91 for connecting the levers 96 and 97 to the pull wires 76 and 77 so that the pull wires can be pulled in accordance with the positioning of the steering lever 96 and locked in place by locking lever 97.

The steering lever 96 is secured to a circular cap 101 which has secured thereto a cylindrical skirt 102 of an eccentric 103. So that the eccentric 103 rotates with the cap 101 as the steering lever 96 is moved. The eccentric 103 is provided with an annular shoulder 104 which rides upon a washer 106 disposed within the part 92. The eccentric 103 is provided with another annular shoulder 107 that engages a shoulder 108 of a lock nut 109 which is threaded onto a cap screw 111. The cap screw 111 is mounted in a circular cap 112 mounted on the housing 91 on the opposite side of the cap 101 and has the locking lever 97 secured thereto. The lock nut 109 is slidably received within a bore 113 provided on a boss 114 formed on the part 93. Means is provided for preventing rotation of the lock nut 109 relative to the boss 114 and consists of a plurality of circumferentially spaced pins 116 that extend into the shoulder 10B of the nut 109 and into the boss 114 to thereby prevent rotation of the look nut 109 but to permit movement longitudinally of the bore 113. A friction washer 121 is provided between the eccentric 103 and the interior of the housing 93. Another friction washer 122 is provided between the head 123 of the nut 109 and skirt 124 of the circular cap 101. O rings 126 and 127 are provided for forming seals between the circular caps 101 and 112 and the housing 91. The eccentric 103 is provided With an annular shoulder 128 which receives the pull wires 76 and 77. The steering lever 96 is provided with a scale 98 with an "0" indicating a center position and the numbers +1 to +2 indicating clockwise (and −1 to −2) indicating counterclockwise movement of the lever from the center position by approximately 45° in each direction from a marker 99 for a total of approximately 90°.

Means is provided for securing the proximal extremities of the pulling wires or elements 76 and 77 in the housing 91 and consists of a holding block 131. The holding block 131 is rectangular in shape and is provided with a pin 132 which is seated within a recess 133. The pull wires 76 and 77 after they leave the eccentric 103 extend forwardly into a lumen 136 of a tension adjustment screw 137 which is provided therewith a slotted adjustment head 138. The adjustment screw 137 is threaded into a nut 141 and is disposed in a slot provided in an H-shaped structure 142 (see FIG. 2) formed integral with the parts 92 and 93. The H-shaped structure 142 includes upstanding leg portions 142 which define a space 143 therebetween and permit adjustment longitudinally of the H-shaped structure 142. From FIG. 2, it can be seen that the coil spring 51 abuts the head 138 of the tension adjustment screw 137. A removable cover 144 is provided in the part 93 to permit access to the head 138 of the adjustment screw 137 to permit adjustment of the tension on the pull wires 76 and 77.

The proximal extremity of the torque tube 31 extends through a twist indicator assembly 151. The twist indicator assembly 151 consists of a housing 152 formed of a suitable material such as plastic. The housing 152 is comprised of an intermediate part 153 which is formed of an opaque plastic and end parts 154 and 156. The end part 154 is secured by suitable means such as an adhesive to a tubular extension 91a of the housing 91. The end part 156 is formed of a transparent plastic and forms an annular bubble chamber 157 which can contain a suitable liquid such as a silicon fluid. A fill plug 158 is provided for filling the bubble chamber 157 and for introducing a small bubble therein in the chamber which can be visible through the transparent end part 156 which will serve to provide a vertical reference for the catheter as hereinafterd described.

The intermediate part of 153 is provided with planar surface 161, which can carry indicia 163 as for example a "0" with numbers +1, +2, +3 on one side of "0" and −1, −2, −3 on the other side of "0" to give an indication as to the extent of rotation or twist of the catheter as hereinafter described. The part 153 is secured to the part 156 by suitable means such as an adhesive and is rotatable therewith of a cylindrical extension 154a of the part 154.

The conductors 63 and 64 extend through the steering handle 26 as shown particularly in FIG. 2 and are disposed beneath the eccentric 103 and in grooves 171 provided in the housing 91 and are connected to cables 172 and 173 which extend through a strain relief fitting 176 mounted in the housing 91 of the steering handle 26. The cable 172 terminates in conductors 177 and 178 which are connected to terminals 179 and 181 (see FIG. 1). Similarly, the cable 173 terminates in two conductors 182 and 183 which are provided with terminals 184 and 186. The terminals 179 and 181 and 184 and 186 are adapted to be plugged into electronic equipment of a conventional type to provide mapping and/or ablation capabilities as well as diagnostic and pacing capabilities for a catheter of the present invention.

Operation and use of the catheter having high torque capacity and method for utilizing the same may now briefly be described as follows. Let it be assumed that it is desired to carry out mapping in a chamber of the heart as for example the right ventricle and thereafter if necessary to carry out an ablation procedure. The catheter can be advanced into the chamber of the heart in a conventional manner as for example, through a femoral artery. The catheter can be advanced into a femoral artery by use of a guiding catheter. The physician while holding the steering handle 26 in one hand introduces the distal extremity of the catheter 21 into the vessel of the patient having a lumen therein. The catheter has sufficient rigidity so that it can be pushed or advanced into the lumen while observing the advancement under a fluoroscope. In view of the fact that the catheter is relatively flexible and small in size, as for example ⅛" or less, it can be readily advanced through the arterial vessel of the patient into a chamber of the heart without damage to the valve of the heart. This is made possible because of digital configuration which can be assumed by the distal extremity of the catheter as shown in dotted lines in FIG. 1.

After it has been determined that the distal extremity of the catheter 21 is in the desired chamber of the heart and the electrodes 28 and 29 are positioned therein, mapping procedures can thereafter be carried out. Typically, a mapping procedure is carried out by bringing the electrodes 28 and 29 into contact with the wall defining a chamber of the heart. As soon as they have been brought into contact with the wall, a potential measurement can be made. The positioning of the distal extremity of the catheter so that the electrodes are brought into contact with the wall forming the chamber is carried out by utilizing the first and second or right and left pull wires or elements 76 and 71 to cause bending of the distal extremity of the catheter in a desired direction. This can be accomplished by operating the steering lever 96 to cause bending of the tip in the desired direction. By way of example the physician can place a J bend in the distal extremity of the catheter. By adjusting the steering lever 96 in accordance with the scale 98 with reference to the mark 99 on the housing 91 as shown in solid lines in FIG. 1. Other bends can be obtained by appropriate adjustment of the steering lever 96. When the desired position is reached, the pull wires 76 and 77 can be locked into the desired position by rotation of the locking lever 97 to fictionally engage the eccentric 103 and hold it in the desired position until the mapping measurement has been completed.

Progressive incremental mapping of the interior of the chamber of the heart can be accomplished by incrementally rotating the distal extremity of the catheter. This is readily accomplished with a catheter of the present invention which has high torque capabilities to make it possible to achieve a one-to-one torquing movement for the distal extremity of the catheter as the steering handle 26 is rotated by the holding hand of the physician. Thus, for example, if it is desired to rotate the distal extremity of the catheter 21 by a suitable incremental rotational movement as for example 5%, this can be accomplished by rotating the steering handle 26 by that amount. The electrodes can then be brought into contact with the wall of the chamber by use of the pull wires 76 and 77 to bend the distal extremity of the catheter by operation of the steering lever 96 by a finger of the holding hand. Another potential measurement can be made. Additional incremental rotation of the distal extremity of the catheter 21 can then be accomplished and thereafter using the pull wires 76 and 77 to achieve appropriate contact with the wall forming the chamber of the heart. Another potential measurement can then be made. In this way the entire circumferential surface defining the chamber can be mapped.

Since the distal extremity of the catheter is relatively flexible, it permits movement of the heart wall during normal beating of the heart even when the distal extremity of the catheter is bent and in contact with the wall of the heart because the catheter will accommodate further bending. Also it should be appreciate by releasing the steering lever 96 and permitting it to return to a "0" position, the distal extremity of the catheter will yieldably engage the wall of the heart and move with the wall of the heart as it moves during normal beating.

The twist indicator 151 which has been provided makes it possible for the physician to keep track of the rotation which he has imparted to the distal extremity of the catheter from a reference position. The bubble in the bubble chamber provides a vertical reference for the scale or indicia 163 appearing on the annular surface 161 of the twist indicator assembly 151. The physician when he believes he has the catheter in a good position which he wishes to use as a reference rotatably adjusts the intermediate part 153 so that the "0" on the scale 163 is in registration with the bubble in the bubble chamber 157. By observing the bubble and the scale 163, the physician is able to keep track of where the catheter is with respect to the "0" reference position previously set. This makes it possible for the physician to know precisely where in a rotational aspect the distal extremity of the catheter 21 is positioned.

The torque tube 31 within the catheter 21 provides very high torque capabilities for the catheter giving a one-to-one torque transmission from the steering handle 26 to the distal extremity of the catheter 21. The construction of the handle is such so that the catheter 21 can be operated with one hand of the physician while the other hand can grasp the handle portion 91a of the steering handle 26 while permitting the fingers of the same hand to operate the steering lever 96 as well as the locking lever 97. The tension adjustment screw 138 is readily adjusted to achieve the desired tension on the pull wires 76 and 77 so that the pull wires 76 and 77 are immediately responsive to the positioning of the steering lever 96 and will cause bending of the distal extremity of the catheter 21 in relatively smooth curves in opposite directions. By observing the scale 98 on the steering lever 96 with respect to the marker 99, the amount of bending and the direction of the bending of the distal extremity of the catheter can be ascertained. By way of example of a certain predetermined scale setting a J bend is placed in the distal extremity of the catheter 21. The physician by knowing those scale settings can obtain predetermined bends by moving the steering lever 96 to scale settings.

The use of the slotted torque tube 31 makes it possible to achieve the desired degree of flexibility within the catheter while still retaining high torque capability of the catheter so that a one to one relationship between movement of the steering handle and the distal extremity of the tip of the catheter can be achieved. These high torque capabilities can be achieved without significantly reducing the longitudinal rigidity of the catheter.

Other embodiments of the invention within the scope of the present invention can utilize different electrode tip configuration to achieve desired diagnostic and pacing functions as well as mapping and/or ablation. In conjunction therewith radio frequency and microwave energy can be utilized when desired.

What is claimed is:

1. A catheter having a high torque capability adapted to be inserted into and through a lumen of a blood vessel comprising a flexible elongate tubular shaft having proximal and distal extremities and a longitudinal axis, said shaft being comprised of a metal torque tube extending substantially through at least a portion of the entire length of the shaft, said metal torque tube having a cylindrical wall with at least one flexible portion therein, said flexible portion being characterized in that at least two longitudinally spaced apart slots are provided in said cylindrical wall subtending an angle of less than 360°, and a flexible non-metallic sleeve of shrink tubing enclosing said metal torque tube and being in contact with the metal torque tube and serving to cover said flexible portion substantially along its entire length and permitting said torque tube to bend in the vicinity of said slots a predetermined amount which is less than that which would create permanent strain in said torque tube, first means on the proximal extremity of the shaft for rotating the shaft about the longitudinal axis by transmitting torque applied to the proximal extremity through the flexible portion and second means on the proximal extremity of the shaft and extending to the distal extremity of the shaft and secured to the distal extremity of the shaft for creating a bending force at the distal extremity to cause bending in the at least one flexible portion.

2. A catheter as in claim 1 together with a handle adapted to be grasped by a human hand and secured to the proximal extremity of said tubular shaft, said handle serving as the first means rotating the tubular shaft.

3. A catheter as in claim 1 wherein said flexible portion is provided with a plurality of longitudinally spaced apart slots subtending angles of less than 360°.

4. A catheter as in claim 1 wherein a plurality of spaced apart flexible portions are provided in the torque tube with the spacing between the portions being greater than a spacing between the slots.

5. A catheter as in claim 3 wherein said slots extend transversely of the torque tube.

6. A catheter as in claim 1 together with an electrode carried by the distal extremity of the shaft.

7. A catheter as in claim 6 together with an additional electrode carried by the distal extremity of the shaft.

8. A catheter having a high torque capability adapted to be inserted into and through a lumen of a blood vessel comprising a flexible elongate tubular shaft having proximal and distal extremities and a longitudinal axis, said shaft being comprised of a torque tube extending through at least a portion of the length of the shaft, said torque tube having a cylindrical wall with at least one flexible portion therein, said flexible portion being characterized in that at least one slot is provided in said cylindrical wall subtending an angle of less than 360°, a flexible sleeve enclosing said torque tube and serving to cover said flexible portion and permitting said torque tube to bend in the vicinity of said slot a predetermined amount which is less than that which would create permanent strain in said torque tube and means secured to said shaft for indicating at the proximal extremity of the shaft the amount of rotation of the shaft about the longitudinal axis.

9. A catheter as in claim 8 wherein said means for indicating the rotation of the shaft includes a bubble chamber having a bubble therein and a scale associated with said bubble chamber for indicating the rotational movement of the shaft with respect to the bubble in the chamber.

10. A catheter having a high torque capability adapted to be inserted into and through a lumen of a blood vessel comprising a flexible elongate tubular shaft having proximal and distal extremities and a longitudinal axis, said shaft being comprised of a torque tube extending at least a portion of the length of the shaft, said torque tube having a cylindrical wall with at least one flexible portion therein, said flexible portion being characterized in that at least one slot is provided in said cylindrical wall subtending an angle of less than 360°, a flexible sleeve enclosing said torque tube and in contact with the torque tube and serving to cover said flexible portion substantially along its entire length and permitting said torque tube to bend in the vicinity of said slot a predetermined amount which is less than that which would create a permanent strain in said torque tube, a handle adapted to be grasped by a human hand and secured to the proximal extremity of said tubular shaft for causing rotation of the tubular shaft, the distal extremity of said shaft having a coil spring therein with a distal extremity which is substantially incompressible in a direction parallel to the longitudinal axis of the shaft, a bendable element having proximal and distal extremities and having the proximal extremity supported by the distal extremity of the substantially incompressible coil spring and having the distal extremity secured to the distal extremity of the shaft, first and second flexible pull elements extending into said shaft and being connected to said bendable element in spaced apart positions on the bendable element distal of the distal extremity of the coil spring a flexible sheath disposed over said bendable element and said first and second flexible pull elements whereby when said pull elements are pulled, the bendable element will bend in a relatively smooth curve.

11. A catheter as in claim 10 together with means carried by the handle and secured to the first and second pull elements for operating said first and second pull elements.

12. A catheter having a high torque capability adapted to be inserted into and through a lumen of a blood vessel comprising a flexible elongate tubular shaft having proximal and distal extremities and a longitudinal axis, said shaft being comprised of a torque tube extending through at least a portion of the length of the shaft, said torque tube having a cylindrical wall with at least one flexible portion therein, said flexible portion being characterized in that at least one slot is provided in said cylindrical wall subtending an angle of less than 360°, a flexible sleeve enclosing said torque tube and serving to cover said flexible portion and permitting said torque tube to bend in the vicinity of said slot a predetermined amount which is less than that which would create permanent strain in said torque tube, a handle adapted to be grasped by a human hand and secured to the proximal extremity of said tubular shaft for causing rotation of the tubular shaft, the distal extremity of said shaft having a coil spring therein which is substantially incompressible in a direction parallel to the longitudinal axis of the shaft, a bendable element having first and second ends and having the first end supported by the substantially incompressible coil spring portion of the flexible tubular element, first and second flexible pull elements extending into said shaft and being connected to said bendable element in spaced apart positions on the bendable element, a flexible sheath disposed over said bendable element and said first and second flexible pull elements whereby when said pull elements are pulled, the bendable element will bend in relatively smooth curves, and means carried by the handle adapted to be engaged by a finger of the hand including a movable member mounted on the handle for operating the pull elements, and scale means disposed in the handle and the movable member for indicating the amount and direction of movement of the movable member relative to the handle and to thereby indicate the curvature which has been placed in the distal extremity of the shaft.

13. A catheter according to claim 12 wherein the slots have a width which determines the maximum amount of bending between one segment and another.

14. A catheter as in claim 13 together with locking lever means carried by the handle adapted to be engaged by a finger of the hand for locking the pull elements in positions to which they have been moved by operating on the pull elements.

15. A catheter having a high torque capability adapted to be inserted into and through a lumen of a blood vessel comprising a flexible elongate tubular shaft having proximal and distal extremities and a longitudinal axis, said shaft being comprised of a torque tube extending through at least a portion of the length of the shaft, said torque tube having a cylindrical well with at least one flexible portion therein, said flexible portion being characterized in that at least one slot is provided in said cylindrical wall subtending an angle of less than 360°, a flexible sleeve enclosing said torque tube and serving to cover said flexible portion and permitting said torque tube to bend in the vicinity of said slot a predetermined amount which is less than that which would create permanent strain in said torque tube, a handle adapted to be grasped by a human hand and secured to the proximal extremity of said tubular shaft for causing rotation of the tubular shaft, the distal extremity of said shaft having a coil spring therein which is substantially incompressible in a direction parallel to the longitudinal axis of the shaft, a bendable element having first and second ends and having the first end supported by the substantially incompressible coil spring portion of the flexible tubular element, first and second flexible pull elements extending into said shaft and being connected to said bendable element in spaced apart positions on the bendable element, a flexible sheath disposed over said bendable element and said first and second flexible pull elements whereby when said pull elements are pulled, the bendable element will bend in relatively smooth curves, means carried by the handle and secured to the first and second pull elements for operating said first and second pull elements, steering lever means carried by the handle and adapted to be engaged by a finger of the hand carrying the handle for operating the pull elements, and means operating on said pull elements including an eccentric coupled to the pull elements and means for securing said eccentric to said steering lever means, said locking lever means including means for preventing rotation of the eccentric when the locking lever means has been moved to a predetermined position with respect to the eccentric.

16. A catheter as inc claim 15 together with means for adjusting the tension on the pull elements.

17. In a method for mapping a chamber in the heart by use of a catheter having proximal and distal extremities and by having at least one electrode carried by the distal extremity, rotating the proximal extremity of the catheter after the distal extremity of the catheter has been positioned in the chamber of the heart by a small incremental distance by bringing the electrode into contact with a wall of the heart and making a potential measurement, thereafter rotating the proximal extremity of the catheter an additional incremental amount, bringing the electrode of the catheter into contact with the wall of the heart and making an additional potential measurement.

18. A method as in claim 17 wherein the electrode is brought into contact with the wall forming the chamber of the heart by bending the distal extremity of the catheter.

19. A method as in claim 18 together with the step of bending the distal extremity of the catheter in first and second directions.

20. A method as in claim 19 wherein said first and second directions are off/set by 180° with respect to each other.

21. A method as in claim 17 together with the step of ascertaining the rotational movement of the proximal extremity of the catheter to thereby ascertain the rotational movement of the distal extremity of the catheter.

22. A method as in claim 17 together with the step of causing the distal extremity of the catheter to track the rotational movement of the proximal extremity of the catheter.

23. A method as in claim 22 together with the step of tracking the rotational movement of the proximal extremity of the catheter.

24. A catheter adapted to be inserted through a lumen of a blood vessel comprising a flexible elongate tubular shaft having proximal and distal extremities and having a longitudinal axis, a handle secured to the proximal extremity of the shaft, and a twist indicator secured to the handle to make it possible to ascertain visually the amount of rotation which has been imparted to the distal extremity of the flexible elongate tubular shaft by rotation of the handle, said twist indicator including a reference on the handle free of the flexible elongate tubular shaft but being rotatably adjustable with respect to the longitudinal axis of the shaft and visual means secured to the handle and which moves as the handle is rotated for indicating the amount of rotation of the handle and the distal extremity of the shaft about the longitudinal axis with respect to the adjusted position of the reference.

25. A catheter as in claim 24 wherein said means for indicating the rotation of the handle includes a bubble chamber having a liquid with a bubble therein secured to the handle and wherein said reference is a rotatable scale carried by the handle in close proximity to the bubble chamber.

26. In a method for indicating the twisting movement of a distal extremity of a catheter comprised of a flexible elongate tubular member having proximal and distal extremities and a longitudinal axis, a bubble chamber and a rotatably adjustable scale mounted on the flexible elongate tubular member, the scale having a zero point and positive and negative indicia on opposite sides of the zero point, the method comprising the steps of positioning the catheter in a predetermined rotational position with respect to the longitudinal axis of the flexible elongate member, observing the location of the bubble in the bubble chamber, adjusting the scale so that the zero on the scale is in registration with the bubble, twisting the proximal extremity of the catheter about the longitudinal axis of the catheter through an angle and ascertaining the amount of angular movement of the catheter by reading the indicium to the scale immediately adjacent the bubble.

27. A catheter adapted to be inserted into and through a lumen of a blood vessel comprising a flexible elongate tubular shaft having proximal and distal extremities and a longitudinal axis, the distal extremity of said shaft having a coil spring therein having a distal extremity which is substantially incompressible in a direction parallel to the longitudinal axis of the shaft, a bendable element having proximal and distal extremities with the proximal extremity supported by the distal extremity of the substantially incompressible coil spring and the distal extremity secured to the distal extremity of the shaft, first and second pull elements extending into said shaft and connected to said bendable element in spaced apart positions on the bendable element distal of the distal extremity of the coil spring and a flexible sheath disposed over said bendable element and said first and second flexible pull elements whereby when said pull elements are pulled, the bendable element will bend in a relatively smooth curve.

28. A catheter as in claim 27 together with a handle adapted to be grasped by a human hand and secured to the proximal extremity of the tubular shaft for causing rotation of the tubular shaft and means carried by the handle and secured to said first and second pull elements for operating said first and second pull elements.

29. A catheter comprising an elongate flexible body having a longitudinal axis, a proximal end and a distal end, at least a portion of the body having a slotted wall segment formed of metal, said slotted wall segment having a plurality of spaced apart slots spaced longitudinally of the longitudinal axis to impart additional flexibility in the slotted wall segment, each of said slots subtending an angle of less than 360°, at least one of said slots being offset radially with respect to another of said slots, a flexible sleeve of shrink tubing enclosing and in contact with said slotted-wall segment permitting the slotted-wall segment to bend along the longitudinal axis, first means on the proximal end of the body for rotating the body about the longitudinal axis and transmitting twisting torque through the slotted wall segment and second means on the proximal end of the body for creating a bending force at the distal end of the body.

30. A catheter as in claim 29 wherein said slotted wall segment is formed of a malleable metal.

31. A catheter comprising a flexible elongate body having a longitudinal axis, a proximal end and a distal end, at least a portion of the body having a slotted wall segment formed of metal, said slotted wall segment having a plurality of slots to impart additional flexibility in the slotted wall segment, each of said slots subtending an angle of less than 360°, a flexible sleeve of shrink tubing enclosing and in contact with said slotted wall segment and permitting the slotted wall segment to bend about the longitudinal axis, first means on the proximal end of the body for rotating the body about the axis by transmitting twisting torque to and through the slotted wall segment and second means on the proximal end of the body and extending to the distal end of the body for creating a bending force at the distal end of the body.

32. A catheter comprising an elongate flexible body having a longitudinal axis, a proximal end and a distal end, said body having first and second spaced apart slotted wall segments, each of said segments having a plurality of slots spaced apart longitudinally of the longitudinal axis and imparting additional flexibility to the slotted wall segment, the spacing between said slotted wall segments being substantially greater than the spacing between slots, a flexible sleeve enclosing the first and second slotted-wall segments and permitting the slotted wall segments to bend about the longitudinal axis, first means on the proximal end of the body for rotating the body about the longitudinal axis and transmitting twisting torque through the first and second slotted wall segments and second means on the proximal end of the body for creating bending forces at the distal extremity of the body.

* * * * *